United States Patent [19]

Greth

[11] 4,143,067
[45] Mar. 6, 1979

[54] PROCESS FOR THE PRODUCTION OF CHLOROACETYL CHLORIDE

[75] Inventor: Erich Greth, Visp, Switzerland

[73] Assignee: Lonza, Ltd., Gampel, Switzerland

[21] Appl. No.: 862,850

[22] Filed: Dec. 21, 1977

[30] Foreign Application Priority Data

Dec. 22, 1976 [CH] Switzerland ................ 16171/76

[51] Int. Cl.$^2$ ............................................. C07C 51/58
[52] U.S. Cl. ............................................. 260/544 Y
[58] Field of Search ................................... 260/544 Y

[56] References Cited

U.S. PATENT DOCUMENTS

| | | | |
|---|---|---|---|
| 2,889,365 | 6/1959 | Prill | 260/544 Y |
| 3,758,569 | 9/1973 | Bissing et al. | 260/544 Y |
| 3,812,183 | 5/1974 | Gash et al. | 260/544 Y |
| 3,882,173 | 5/1975 | Gash et al. | 260/544 Y |

FOREIGN PATENT DOCUMENTS 782773 9/1957 United Kingdom ................ 260/544 Y

OTHER PUBLICATIONS

Groggins, "Unit Processes in Organic Synthesis," pp. 177–178, 224–226, (1952).

*Primary Examiner*—Gerald A. Schwartz
*Attorney, Agent, or Firm*—Fisher, Christen & Sabol

[57] ABSTRACT

Process for the production of chloroacetyl chloride. In the process ketene is reacted with sulfuryl chloride in a solvent at a temperature of −40° to +40° C. to produce chloroacetyl chloride. Up to, and including, one mole of ketene is used per mole of sulfuryl chloride. The product contains very low levels of dichloroacetyl chloride as a contaminant.

8 Claims, No Drawings

PROCESS FOR THE PRODUCTION OF CHLOROACETYL CHLORIDE

BACKGROUND OF THIS INVENTION

1. Field of This Invention

This invention relates to a process for the production of chloroacetyl chloride.

2. Prior Art

The production of chloroacetyl chloride (CAC) by conversion of ketene with chlorine in widely diverse solvents is known. Examples of such solvents are alkylacetate (British Pat. No. 782,773), $SO_2$ (U.S. Pat. No. 2,889,365), alicyclic carbonate, alkoxyalkyl ester, glycol ester (German OS No. 2,247,764), sulfones (U.S. Pat. No. 3,882,173), phosphate ester (U.S. Pat. No. 3,883,589) and lactones (German OS No. 2,247,765). When most of these solvents are used, dichloroacetyl chloride (DCAC) is obtained as a by-product in quantities of 2 to 6.5 percent. However, since the presence of a large portion of dichloroacetyl chloride in chloroacetyl chloride is detrimental in many types of usage, the art nowadays requests chloroacetyl chloride containing only 0.1 to 0.3 percent of dichloroacetyl chloride. The removal of dichloroacetyl chloride from chloroacetyl chloride by simple distillation is virtually impossible because they have essentially equal boiling points.

U.S. Pat. No. 3,763,023 teaches separation by means of azeotropic distillation. Azeotropic distillation has various disadvantages, such as, high investment requirements, high operating costs and sensitivity to fluctuations in product composition.

When lactones or phosphate esters are used as solvents, the desired low levels of dichloroacetyl chloride are achieved. But there are disadvantages in the use of such solvents as they are relatively expensive and such solvents cannot be completely recovered. The losses of solvent are relatively great — experiments resulted in losses of 10 to 15 percent, depending on the lactone or phosphate ester used.

Dichloroacetyl chloride has been removed by chemical conversion with water or alcohols, whereby the dichloroacetyl chloride preferably reacts to dichloroacetic acid or ester (German Pat. No. 2,313,405). Since this reaction however is not selective and chloroacetyl chloride can enter into the reaction, a high degree of loss of chloroacetyl chloride results.

BROAD DESCRIPTION OF THIS INVENTION

An object of this invention is to provide a process for the production of chloroacetyl chloride which contains a low level of dichloroacetyl chloride contaminant. Other objects and advantages of this invention are stated elsewhere herein or are obvious herefrom to one ordinarily skilled in the art.

The objects and advantages of this invention are achieved by the process of this invention.

This invention is based on the task of avoiding the disadvantages of the known processes and of making accessible chloroacetyl chloride, which preferably contains less than 0.3 percent dichloroacetyl chloride, in a simple manner and without large losses of solvent. This is achieved according to this invention by reacting ketene with sulfuryl chloride in a solvent at a temperature of $-40°$ to $+40°$ C. to produce chloroacetyl chloride. Up to 1 mole of ketene per mole of sulfuryl chloride is used.

The process of this invention can be carried out by dissolving sulfuryl chloride in a solvent and introducing ketene into the mixture and by allowing the reactants to react to produce chloroacetyl chloride, or may be conducted by introducing at the same time the ketene and sulfuryl chloride put into the solvent and allowing them to react to produce chloroacetyl chloride.

The chlorination of ketene with sulfuryl chloride (i.e., production of chloroacetyl chloride) may be produced on the basis of the following formula:

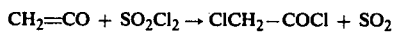

$$CH_2=CO + SO_2Cl_2 \rightarrow ClCH_2-COCl + SO_2$$

Preferably the reaction temperature is from $-20°$ to $+20°$ C.

According to the reaction formula one mole of sulfuryl chloride is needed for one mole of ketene and this probably is the optimum ratio of ketene and $SO_2Cl_2$. However, it is difficult to precisely dose in an exact molar quantity of ketene; therefore one effectively operates with a slight deficiency of ketene. This method of operation is not a disadvantage since the unreacted sulfuryl chloride may be separated and used again. On the other hand, an excess of ketene should be avoided since the excess of ketene reacts with chloroacetyl chloride in an insertion reaction which leads to a decrease of the yield.

Preferably 0.5 to 1 mole of ketene per mole of sulfuryl chloride is used. More preferably 0.8 to 1 mole of ketene per mole of sulfuryl chloride is used.

The choice of the solvent is limited by the fact that the solvent must not react with the sulfuryl chloride, for example, all protic solvents, and must not react with the chloroacetyl chloride, for example, dimethyl formamide.

A series of solvents such as acetylchloride, chloroacetyl chloride, nitro benzol, chlorobenzol, benzonitrile, chloroform and methylene chloride are likewise not very well suited for the reaction since their use results in poor yields of chloroacetyl chloride, and, in many cases, high dichloroacetyl chloride content appears in the end product.

Esters, lactones, carbonates, trialkylphosphates or sulfones are suitable solvents for use in the reaction of this invention. Within these groups and for practical reasons, solvents, which have a boiling point similar to that of chloroacetyl chloride, for example, ethyl esters of acetic acid of that description, are out of the question without however the rest of such groups being excluded from this invention. Examples of suitable solvents are acetic acid methyl ester, acetic acid benzyl ester, succinic acid diethyl ester, chloroacetic ester, glycol diacetate, butyro-lactone, triethylphosphate, sulfolane and propylene carbonate. Preferably the solvent is acetic acid methyl ester.

The suitable solvents for for this invention may be defined by the donor number as a physical constant. The donor number is defined as a solvent physical constant by V. Gutmann, "Coordination Chemistry in Non-Aqueous Solutions", Springer-Verlag, Vienna — New York, (1968), as:

$$DN_{SbCl_5} = -\Delta H_{D.SbCl_5}$$

i.e., the donor number $DN_{SbCl_5}$ is the negative reaction enthalpy of a donor solvent with antimony pentachloride measured in 1,2-dichloroethane. Effectively solvents defined by a donor number between 15 and 23 are used.

The quantity of solvent in relation to the reaction partners is not per se criticial. With a rising quantity of solvent, the content of dichloroacetyl chloride drops in relation to the chloroacetyl chloride.

Preferably a ratio of sulfuryl chloride to solvent of 1:0.5 to 1:4 is maintained.

The reaction may be carried out in different ways. As the most simple method of operation, ketene is introduced into sulfuryl chloride dissolved in a solvent. After completion of the reaction, SO₂ may be removed from the reaction chamber and then the solvent is separated from the reaction mixture.

Examination of the reaction however has shown that circumstances are favorable for the prevention of dichloroacetyl chloride formation whenever an excess of $SO_2Cl_2$ is avoided by introducing the sulfuryl chloride in a corresponding molar ratio to the ketene in a solvent or by continuously adding together the ketene and solvent containing sulfuryl chloride in corresponding ratios.

It is also advantageous to prevent a too strong of enrichment SO₂ in the reaction mixture by periodically or continuously removing the SO₂ formed from the reaction chamber.

The resultant sulfur oxide can easily be converted back to sulfuryl chloride according to known processes by treatment with chlorine [for example, on activated charcoal or with organic substances (camphor) as catalysts] into sulfuryl chloride:

$$SO_2 + Cl_2 \rightarrow SO_2Cl_2$$

Thus, for this process one needs only ketene and chlorine since the sulfuryl chloride serves as a carrier for the chlorine and may be circulated.

Another method of operation is possible. The solvents used according to this invention catalyze the reaction of SO₂ and chlorine into $SO_2Cl_2$. This permits in a simple manner a process of mixing SO₂ in a solvent in a first (preliminary) reaction vessel with chlorine for continuous production into $SO_2Cl_2$. This solution is treated in the main reaction vessel with ketene, according to the process of this invention. After separation of the chloroacetyl chloride, the solvent and the SO₂ developing during the reaction can be circulated.

An advantage of the process of this invention consists in the fact that less undesirable dichloroacetyl chloride develops than in the case of direct chlorination of ketene with elementary chlorine. According to the process of this invention, chloroacetyl chloride is obtained with dichloroacetyl chloride contents of below 0.1 to 0.3 percent. In the case of such pure products, any further separation operation of dichloroacetyl chloride from chloroacetyl chloride is superfluous.

DETAILED DESCRIPTION OF THIS INVENTION

As used in this specification (including the claims), all ratios, percentages and parts are on a weight basis, unless otherwise stated or otherwise obvious herefrom by one ordinarily skilled in the art.

EXAMPLE 1

128.7 gm. of ketene (3.062 mole) was introduced over a 1 hour period into a solution of 460.1 gm. of sulfuryl chloride in 448.2 gm of acetic acid methyl ester while stirring. As a result of outside cooling with a cryomate, the temperature was kept at −22° C. After completion of the introduction of ketene, the mixture was brought to room temperature and distilled via a slit tube column (collimator column). 291.54 gm. of a mixture of 290.83 gm. of chloroacetyl chloride and 0.714 gm. of dichloroacetyl chloride was obtained. The content of dichloroacetyl chloride was 0.245 percent by weight; and the yield of chloroacetyl chloride (related to ketene used) was 84.11 percent.

EXAMPLE 2

Example 1 was repeated with 120.22 gm. of acetic acid methyl ester, 124.25 gm. of sulfuryl chloride and 34.43 gm. of ketene (0.819 mole). Only now the sulfuryl chloride was also added drop by drop from a dripping funnel during a one hour period. After distillation, a mixture of 77.74 gm. of chloroacetyl chloride and 0.112 gm. of dichloroacetyl chloride was obtained. The content of dichloroacetyl chloride was 0.144 percent by weight; and the yield of chloroacetyl chloride was 84.05 percent.

EXAMPLE 3

Example 1 was repeated with 114.27 gm. of sulfuryl chloride, 114.34 gm of acetic acid methyl ester and 31.99 gm. of ketene (0.761 mole). But the introduction of ketene was interrupted four times and the resultant sulfur oxide was sucked off by application of a vacuum of 10 torr. After distillation, 71.59 gm. of chloroacetyl chloride and 0.065 gm. of dichloroacetyl chloride were obtained. The content of dichloroacetyl chloride was 0.091 percent by weight; and the yield of chloroacetyl chloride was 83.30 percent.

EXAMPLE 4

Example 2 was repeated with 120.67 gm. of acetic acid methyl ester, 136.32 gm. of sulfuryl chloride and 37.61 gm. of ketene (0.880 mole). But the temperature was kept at 17° to 18° C. by cooling with ice water. 85.39 gm. of chloroacetyl chloride and 0.235 gm. of dichloroacetyl chloride were obtained. The content of dichloroacetyl chloride was 0.274 percent; and the yield of chloroacetyl chloride was 85.88 percent (related to the ketene used).

In Table 1 the results in other solvents have been summarized. All experiments were carried out at −20° C. according to the method of operation of Example 1. For each solvent used, the content of dichloroacetyl chloride (in percent by weight related to the sum of chloroacetyl chloride and dichloroacetyl chloride) and the chloroacetyl chloride yield in percent by weight (related to the ketene used) are given:

TABLE I

| Solvent | Dichloroacetyl Chloride content, Percent | Chloroacetyl Chloride Yield, Percent |
|---|---|---|
| acetic acid benzyl ester | 0.06 | 68.63 |
| butylacetate | 0.26 | 76.60 |
| glycol diacetate | 0.43 | 68.00 |
| succinic acid diethyl ester | 0.80 | 65.00 |
| chloroacetic ester | 0.30 | 79.80 |
| butyrolacetone | 0.06 | 79.80 |
| triethyl phosphate | 0.20 | 69.05 |
| sulfolane | 0.51 | 74.40 |
| propylene carbonate | 0.19 | 78.70 |

TABLE II

| Solvent | Reaction Temperature | Dichloroacetyl Chloride content, Percent | Chloroacetyl Chloride, Yield Percent |
|---|---|---|---|
| acetic acid | +20° C. | 0.34 | 90.4 |

TABLE II-continued

| Solvent | Reaction Temperature | Dichloroacetyl Chloride content, Percent | Chloroacetyl Chloride, Yield Percent |
| --- | --- | --- | --- |
| methyl ester | | 0.41 | 91.4 |
| butyrolactone, | +15° C. | 0.05 | 77.6 |
| | | 0.07 | 79.3 |
| propylene carbonate | +15° C. | 0.33 | 84.3 |
| | | 0.38 | 87.6 |
| propylene carbonate | +40° C. | 0.58 | 82.9 |
| | | 0.60 | 84.9 |

What is claimed is:

1. A process for the production of chloroacetyl chloride which comprises reacting ketene with sulfuryl chloride in a solvent at a temperature of −40° to +40° C. to produce chloroacetyl chloride 0.4 to 1 mole of ketene being used per mole of sulfuryl chloride.

2. Process as claimed in claim 1 wherein the sulfuryl chloride is dissolved in a solvent, ketene is introduced into such mixture and the reactants are allowed to react to produce chloroacetyl chloride.

3. Process as claimed in claim 1 wherein the solvent is placed in a reaction chamber, the ketene and sulfuryl chloride are introduced simultaneously into the solvent and the ketene and sulfuryl chloride are allowed to react to produce chloroacetyl chloride.

4. Process as claimed in claim 1 wherein the $SO_2$ developing during the reaction is periodically or continuously removed from the reaction chamber during the reaction.

5. Process as claimed in claim 1 wherein the solvent has a donor number between 15 and 23.

6. Process as claimed in claim 1 wherein acetic acid methyl ester is used as the solvent.

7. Process as claimed in claim 1 wherein the reaction is carried out at a temperature of −20° C. to +20° C.

8. Process as claimed in claim 1 wherein 0.8 to 1 mole of ketene is used per mole of sulfuryl chloride.

* * * * *